United States Patent [19]
Hsu et al.

[11] Patent Number: 6,093,170
[45] Date of Patent: Jul. 25, 2000

[54] STRUCTURE SAFETY SYRINGE

[76] Inventors: Kuo-Chi Hsu, No. 206, Lane 125, Sec. 3, Yuan-Gi Road, Yuan-Lin Chen, Chang-Hua Hsien; Deng-Tzong Lin, No. 214-2, Sec. 2, Chung-Shan Road, Chang-Hua City, both of Taiwan

[21] Appl. No.: 09/401,266

[22] Filed: Sep. 23, 1999

[30] Foreign Application Priority Data

Jan. 28, 1999 [TW] Taiwan .................................. 88201422

[51] Int. Cl.$^7$ ...................................................... A61M 5/00
[52] U.S. Cl. ........................... 604/110; 604/192; 604/218; 604/263
[58] Field of Search .................................... 604/110, 187, 604/192, 198, 263, 218

[56] References Cited

U.S. PATENT DOCUMENTS

| | | | |
|---|---|---|---|
| 4,816,022 | 3/1989 | Poncy | 604/198 |
| 5,222,945 | 6/1993 | Basnight | 604/110 |
| 5,279,579 | 1/1994 | D'Amico | 604/192 |
| 5,318,547 | 6/1994 | Altschuler | 604/263 X |
| 5,415,645 | 5/1995 | Friend et al. | 604/110 |

*Primary Examiner*—John D. Yasko
*Attorney, Agent, or Firm*—Bacon & Thomas

[57] ABSTRACT

An improved structure safety syringe comprised of a barrel having two trapezoidal-shaped tabs, a sleeve with a guide slot and, furthermore, limit slots extending from the circumferential surface at the two ends of the guide slot and an insertion section is formed at the inside end of the limit slot, wherein utilizing the engagement of the tabs and the insertion section enables the positioning of the barrel and the sleeve, and a plunger having a protective cap at the force application end that can be broken off at an appropriate time. When the protective cap is broken off and, furthermore, inserted into the other end of the sleeve, the objective of positioning is achieved and, furthermore, ensures that the hypodermic needle is not exposed.

5 Claims, 8 Drawing Sheets

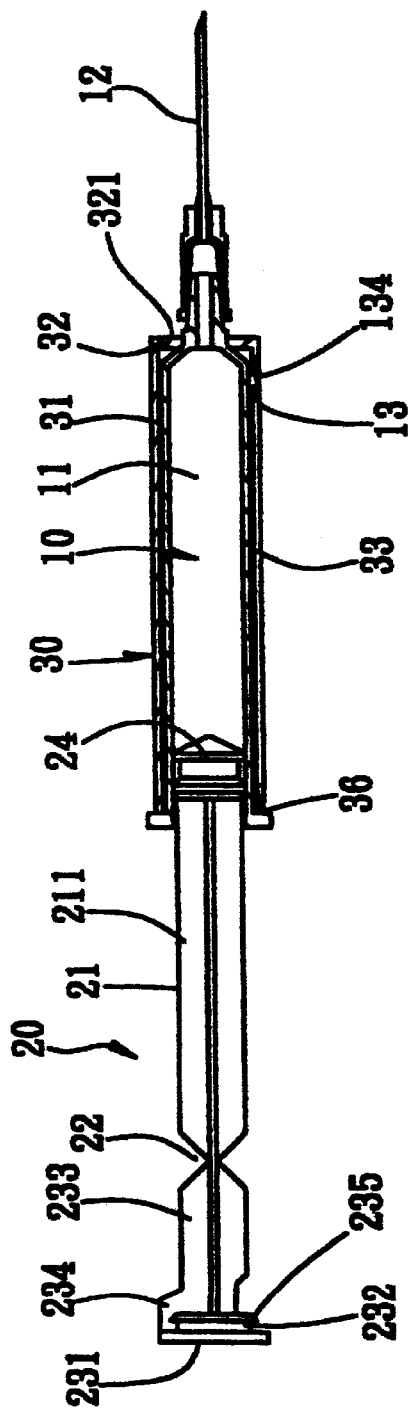
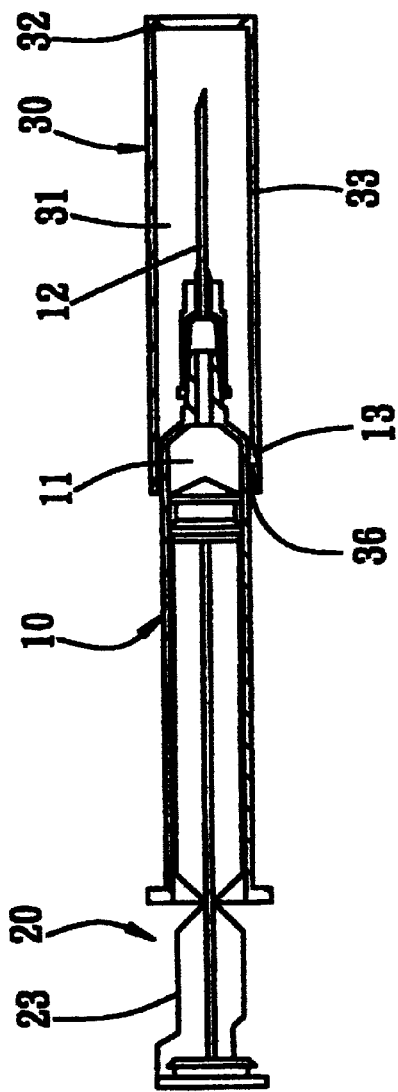
FIG3
FIG4

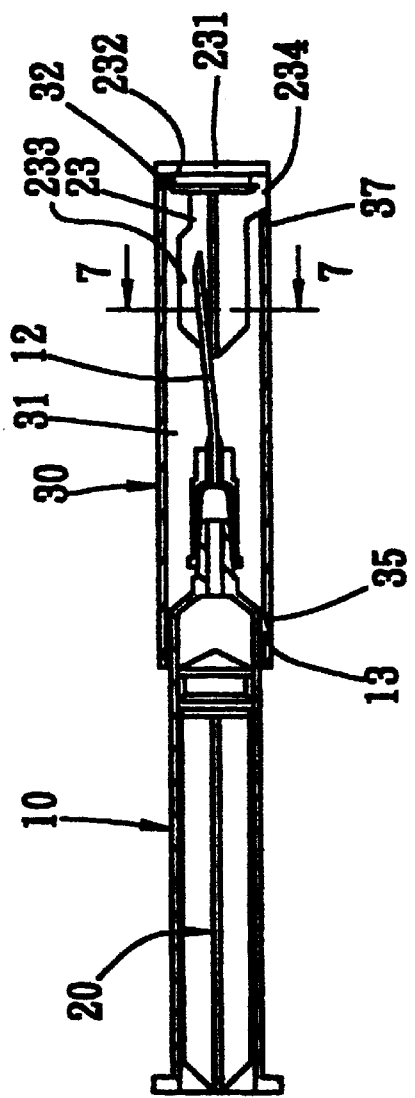
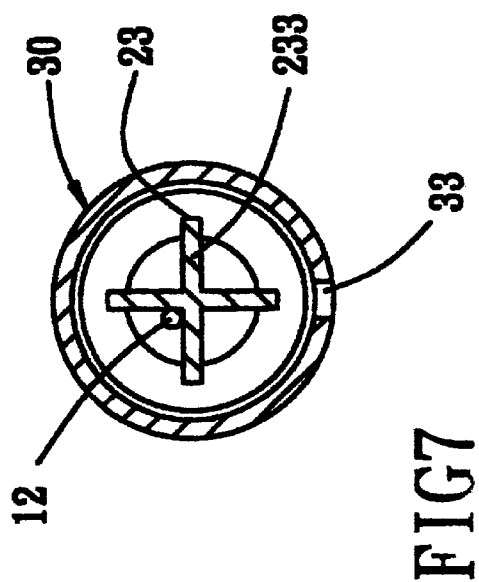

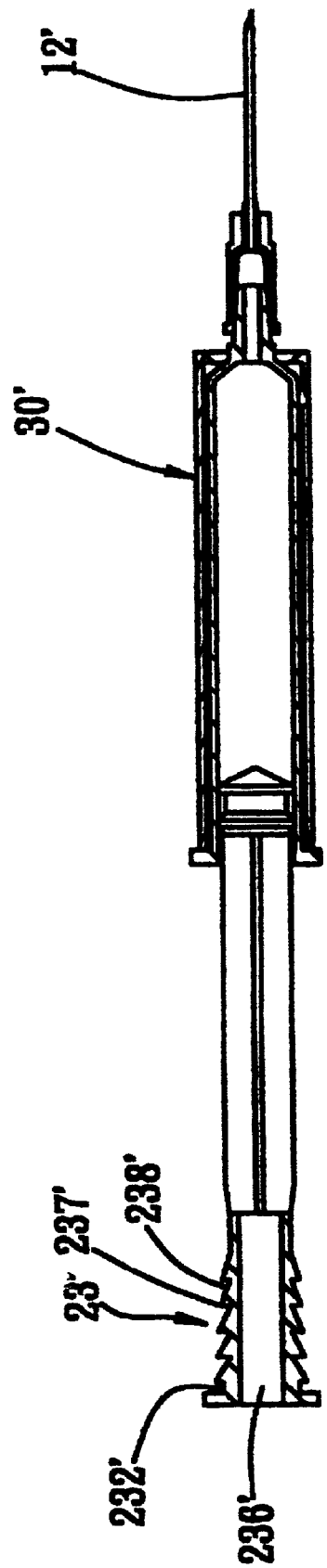
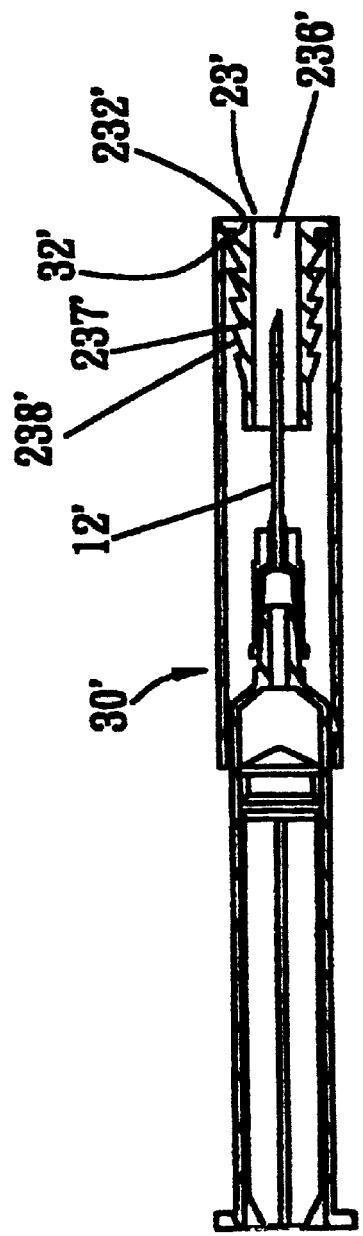
FIG 9
FIG 10

STRUCTURE SAFETY SYRINGE

BACKGROUND OF THE INVENTION

1) Field of the Invention

The invention herein relates to an improved structure safety syringe that is simple, easy to operate, and offers a high degree of utilization safety.

2) Description of the Prior Art

Since AIDS, hepatitis type A, and hepatitis type B are transmitted by the re-use of hypodermic needles, the use of disposable needles is the basic safeguard in preventing the spread of such communicable diseases.

While the use of disposable hypodermic needles ensures the safety of the persons receiving injections, medical treatment personnel face substantial risks, especially after administering injections to patients. When a hypodermic needle is placed back into its cover, a self-inflicted puncture can easily occur due to accidental impact or carelessness. To minimize such hazardous situations, a safer type of syringe has now been successfully developed (new patent application No. 86,214,720). As indicated in FIG. 1, the said syringe is comprised of a barrel 1, a sleeve 2, and a plunger 3; the said barrel 1 is of a hollow cylindrical construction and has a hypodermic needle 4 installed at one end and a one-way plunger opening 101 at the other end; a short round tab 102 is disposed on the circumferential surfaces at the two sides of the barrel 1 near the hypodermic needle 4; two guide slots 201 are formed lengthwise along the walled surface of the said sleeve 2, a limit slot 202 extends from the circumferential surface at the two ends of the said guide slots 201 and, furthermore, the limit slots 202 and the guide slots 201 merge perpendicularly, and a sleeve opening 203 is formed inside the sleeve 2 and, furthermore, a notch 204 that extends up to the limit slot 202 is formed along the annular surface of the sleeve opening 203 of the sleeve 2; as such, when the barrel 1 is inserted into the sleeve opening 203 of the sleeve 2, the tab 102 situated along the notch 204 is inserted into the guide slot 201; furthermore, after the injection is administered, the operator pulls the sleeve 2 over the barrel 1 and, furthermore, with the tab 102 now positioned at one end of the guide slot 201, rotates it an appropriate number of degrees, causing the tab 102 to move into the limit slot 202, thereby preventing the separation of the sleeve 2 and the barrel 1 and, furthermore, causes the hypodermic needle 4 to be housed within the sleeve 2 to achieve the objective of safety.

However, when the tab 102 is moved into the limit slot 202, the limit slot 202 does not provide any effective positional latching such that the sleeve 2 is easily rotated over the barrel 1 in the opposite direction for an appropriate number of degrees and, therefore, the sleeve 2 may slip back and, furthermore; cause the hazardous exposure of the hypodermic needle 4.

Additionally, since the sleeve 2 is constructed of a plastic material, it readily deforms when subjected to squeezing, at which time the hypodermic needle 4 may protrude out of the guide slot 201, resulting in the hazardous infliction of a puncture wound.

In view of the said situation, the inventor of the invention herein devoted extensive thought to the matter and, furthermore, conducted many years of research, development, and testing which culminated in the successful completion of the present invention.

SUMMARY OF THE INVENTION

The primary objective of the invention herein is to provide an improved structure safety syringe in which the sleeve can be pulled and, furthermore, cover the hypodermic needle by enabling the barrel and the sleeve to become latched into position and thereby achieve the objective of utilization safety.

Another objective of the invention herein is to provide an improved structure safety syringe in which after the plunger is utilized, the protective cap is broken off at the force application end and, furthermore, inserted into the end of the sleeve and then positionally latched to the sleeve, thereby further preventing the hypodermic needle from becoming exposed.

Therefore, based on the improved structure safety syringe provided by the invention herein, the said syringe has a plunger that is inserted into the plunger opening of the barrel and, furthermore, a hypodermic needle is installed at one end and a hollow tubular sleeve is fitted over the exterior section of the barrel; wherein, a tab is disposed near the hypodermic needle on the two sides of the circumferential surface of the barrel, with the said tab being of a trapezoidal shape having an insertion end formed at one end and a catch section formed at the other end and, furthermore, an angled leading surface is formed on two sides, with the said angled leading surface gradually expanding outward in angle as it proceeds from the insertion end to the catch end; a slanted surface is formed on the top surface of the tab and the said slanted surface is aligned with lower side of the hypodermic needle; the said sleeve is of a hollow tubular construction having a sleeve opening inside, a binding-type mounting ring is formed at one end of the sleeve opening and furthermore, two guide slots are disposed lengthwise along the walled face of the sleeve and a limit slot extends from along the circumferential surface at the two ends of the said guide slot, wherein an insertion section is formed at the inner ends of the limit slot, and a stop section projects towards the limit slot in each of the openings between the said insertion sections and limit and, furthermore, enabling the width between the two stop sections to be smaller than the width of the barrel catch end such that the said tab 13 is insertable between the two stop sections and remains inserted in a fixed position in the said insertion sections; there is a protective cap capable of being broken off at an appropriate time proximal to the force application end of the said plunger and a groove is formed at the inner side of the press plate of the said protective cap such that when the protective cap is broken and, furthermore, inserted into the end of the sleeve having the mounting ring, the said groove become engaged onto the mounting ring of the sleeve, thereby achieving the objective of positioning of the protective cap.

The technology, methods, and functions utilized by the invention herein are presented in the brief description of the drawings below followed by the detailed description of the preferred embodiments to enable a further understanding of the objectives, structure, and innovations of the invention herein.

BRIEF DESCRIPTION OF THE DRAWINGS

FIG. 3 is a cross-sectional drawing of the said preferred embodiment of the invention herein in the utilization state.

FIG. 4 is a cross-sectional drawing of the said preferred embodiment of the invention herein in the post-utilization state.

FIG. 6 is a cross-sectional drawing of the positioned protective cap of the said preferred embodiment of the invention herein.

FIG. 7 is a cross-sectional drawing of the positioned protective cap of the said preferred embodiment of the invention herein as viewed from the end.

FIG. 9 is a cross-sectional drawing of the second preferred embodiment of the invention herein in the utilization state.

FIG. 10 is a cross-sectional drawing of the positioned protective cap of the second preferred embodiment of the invention herein.

DETAILED DESCRIPTION OF THE PREFERRED EMBODIMENTS

Figure 1:
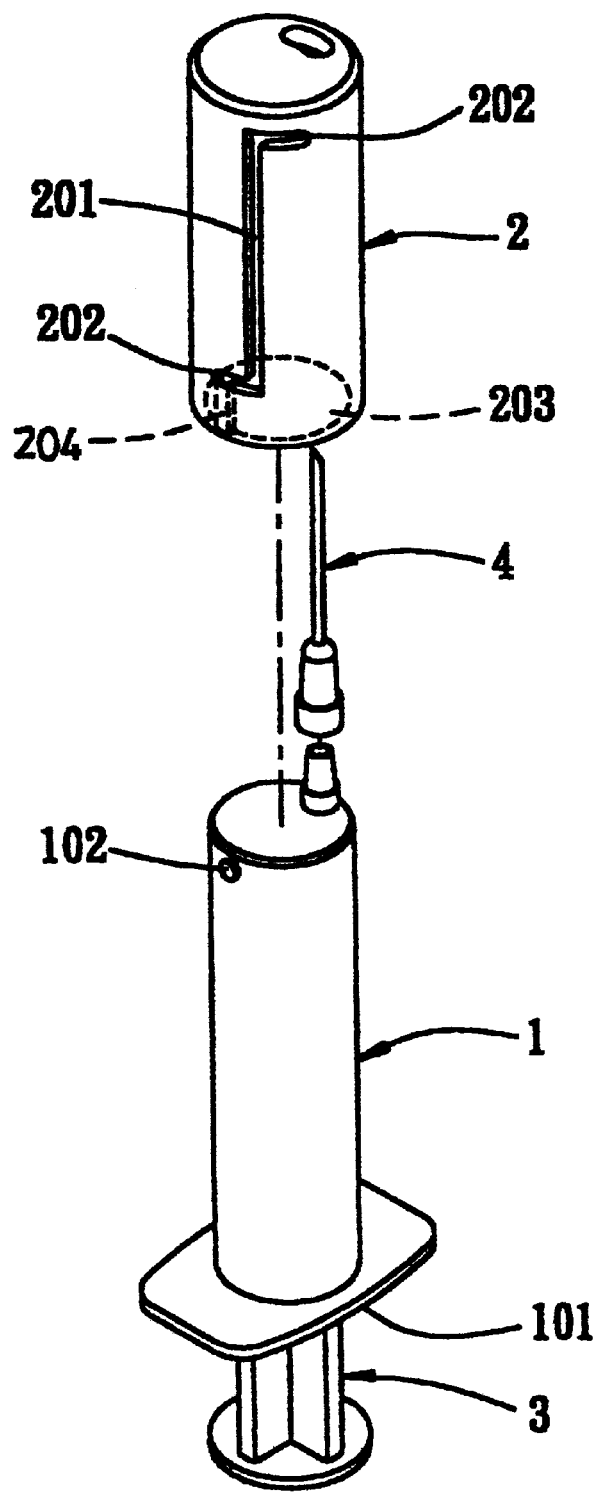
FIG. 1 is an exploded drawing of a conventional syringe needle tube.
Figure 2:
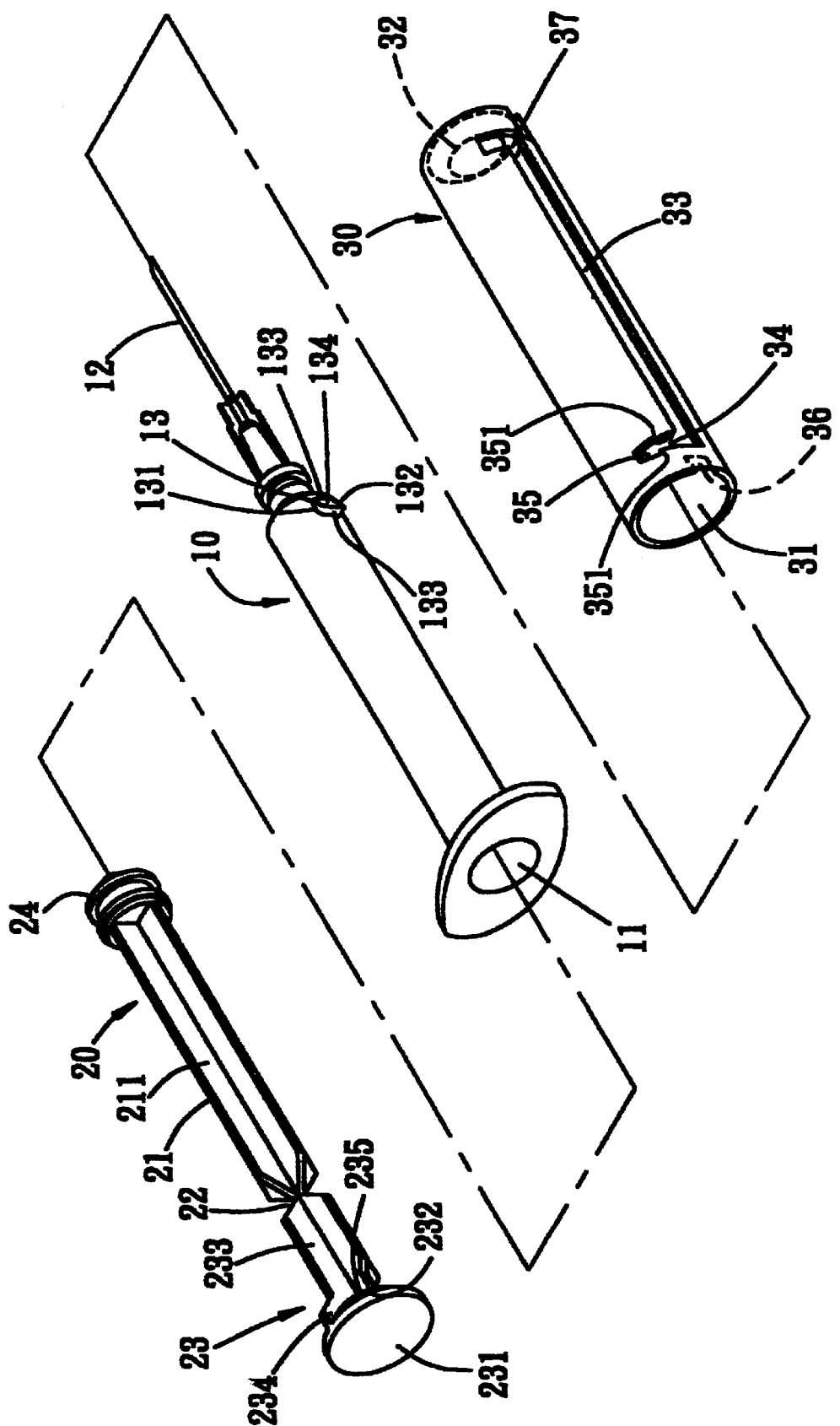
FIG. 2 is an exploded drawing of the preferred embodiment of the invention herein.

Referring to FIG. 2 and FIG. 3, the improved structure safety syringe of the invention herein is comprised of a barrel 10, a plunger 20, and a sleeve 30 of which:

The said barrel 10 is of a hollow cylindrical construction having a one-way plunger opening 11 through the interior section and a hypodermic needle 12 attached to the sealed exterior section of the end; a tab 13 is disposed near the hypodermic needle 12 on one side of the circumferential surface of the barrel 10, with the said tab 13 being of a trapezoidal shape and having an insertion end 131 formed at one extremity and a catch section 132 formed at the other end and, furthermore, the width of the catch section 132 is larger than that of the insertion end 131 and an angled leading surface 133 is formed on two sides, with the said angled leading surface 133 gradually expanding outward in angle as it proceeds from the insertion end 131 to the catch end 132; a slanted surface 134 is formed on the top surface of the tab 13 and the said slanted surface 134 is aligned with lower side of the hypodermic needle 12.

The said plunger 20 is inserted into the plunger opening 11 of the barrel 10 and the plunger member 21 consists of four plunger elements 211 radiating diametrically in a perpendicular arrangement and, furthermore, causing it to be sectionally cross-shaped; notches 22 are formed at the approximate rear extent of the plunger member 21, with the notches 22 constituting the breakable area of the plunger member 21; and a protective cap 23 is formed behind the breakable area; the said protective cap 23 consists of a press plate 231 having a groove 232 formed on its interior lateral surface and the perpendicularly configured four plunger elements 211 proceeding lengthwise from the interior side of the groove 232, wherein a latch section 234 projects outward at the rear of the press plate 231, a beveled surface 235 of a gradually reduced circumference is formed on the outer side of the groove 232, and a rubber sleeve 24 is positioned at the front end of the said plunger 20.

The said sleeve 30 is of a hollow tubular construction having a sleeve opening 31 inside, a binding-type mounting ring 32 is formed at one end of the sleeve opening 31 and an angled leading surface 321 is formed on the exterior lateral surface of the said mounting ring 32 and, furthermore, a guide slot 33 is disposed lengthwise along the walled face of the sleeve 30 and a limit slot 34 extends along the circumferential surface at the two ends of the said guide slot 33, wherein an insertion section 35 aligned with the tab 13 is formed at the interior ends of the said guide slot 33, a triangular-shaped stop section 351 projects towards the limit slot 34 in each of the openings between the said insertion sections 35 and the limit slots 34 and, furthermore, enabling the width between the two stop sections 351 to be smaller than the width of the barrel 10 catch end 132 such that the said tab 13 as insertable between the two stop sections 351 and remains inserted in a fixed position in the said insertion sections 35; additionally, an angled leading surface 36 aligned with the said guide slot 33 is formed on the interior annular surface at one end of the sleeve opening 31 of the said sleeve 30 and, furthermore, enabling the said angled leading surface 36 to gradually increase outwardly in angle, and a catch slot 37 of an appropriate length and, furthermore, open in a single direction is formed in the circumferential surface at one end of the mounting ring 32 such that when the mounting ring 32 on the sleeve 30 is over the protective cap 23 as it is broken, the said latch section 234 is engaged into the catch slot 37, thereby enabling positioning over the protective cap 23 and, furthermore, without giving rise to rotation by the sleeve 30.

Having described the structural components and their relative locations of the improved structure safety syringe of the invention herein, the functions achievable by the present invention are elaborated as follows:

As indicated in FIG. 3, when the fabrication of all the structural components are completed and, furthermore, assembly is conducted, the tab 13 is aligned with the angled leading surface 36 and, furthermore, to enable the placement of the mounting ring 32 at one end of the sleeve 30 sleeve opening 31 over the end of the barrel 10 having the hypodermic needle 12, the slanted surface 134 formed on the top surface of the tab 13 and the angled leading surface 36 serve as a means of guidance, thereby enabling the tab 13 to readily enter the sleeve opening 31 and finally become inserted in the guide slot 33 and, furthermore, the rubber piston 24 at one end of the plunger 20 is inserted into the plunger opening 11 of the barrel 10; at this stage, the plunger 20 can be pulled and pushed along the plunger opening 11 to achieve injection and the blood aspiration capability.

Figure 5:
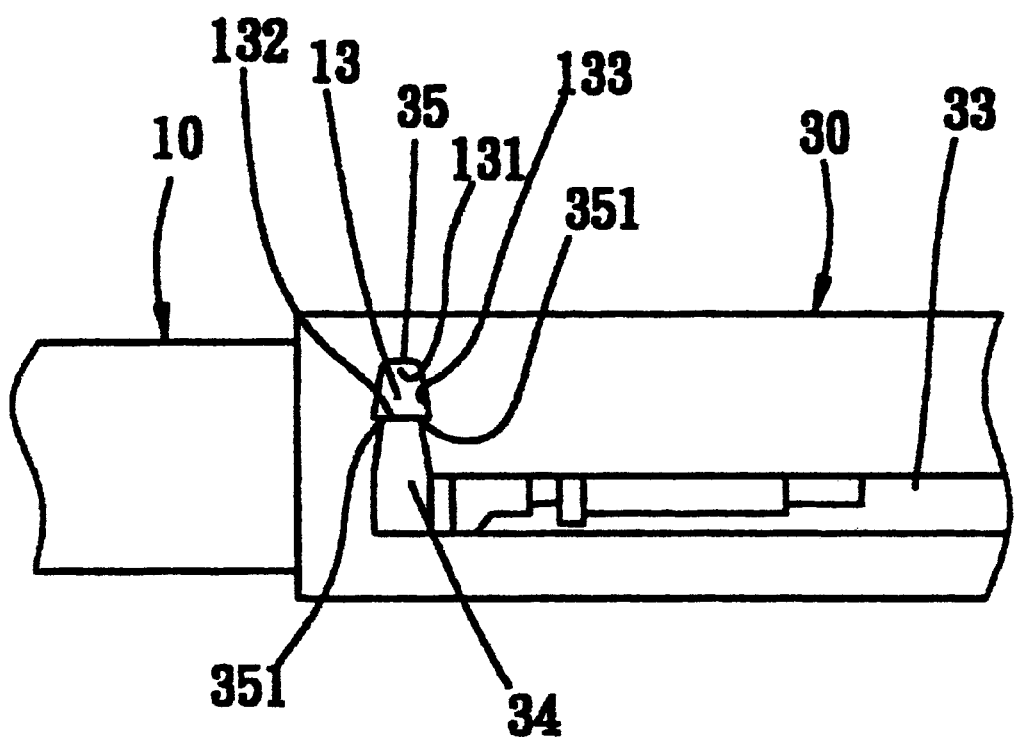
FIG. 5 is a drawing of the tab and insertion section of the insertion sleeve.

Referring to FIG. 4 and FIG. 5, when use of the syringe is completed and, furthermore, the unit is to be discarded, the operating personnel rotates the sleeve 30 an appropriate number of degrees over the barrel 10, causing the movement of the tab 13 to the limit slot 34 at one side of the guide slot 33, at which time the sleeve 30 is then pulled outwards and, utilizing guiding action of the tab 13 and the guide slot 33, the tab 13 is moved to the other end of the guide slot 33, at which time, the sleeve 30 is then rotated an appropriate number of degrees, causing the insertion end 131 of the tab 13 to become engaged between the two stop sections 351 and, furthermore, utilizing the guiding action of the angled leading surface 133 and the material properties of the sleeve 30 itself, the tab 13 readily becomes ensconced in the insertion section 35 and, furthermore, utilizing the stop section 351 and the catch section 132 in coordination prevents the sleeve 30 from readily rotating over the barrel 10, thereby ensuring that the hypodermic needle 12 will not become hazardously exposed.

Referring to FIG. 6 and FIG. 7, to further increase the level of safety, with the protective cap 23 extending from the exterior section of plunger opening 11, the operating personnel can break it off at the notches 22 to produce a protective cap 23 and, furthermore, after the latch section 234 of the protective cap 23 is aligned with the catch slot 37 of the sleeve 30, it is pressed into the front end of the sleeve 30 and, furthermore, causes the mounting ring 32 to become engaged in the groove 232 and the latch section 234 to become inserted into position in the catch slot 37, thereby sealing the front end of the sleeve 30, while ensuring that the said protective cap 23 and the sleeve 30 are incapable of rotation and the hypodermic needle 12 remains in a fixed position at the junction of the plunger elements 233 and, furthermore, the hypodermic needle 12 cannot be moved or protrude from the guide slot 33 by rotating the protective cap 23 to thereby achieve a superior protective function.

Therefore, the sleeve 30 is already installed on the barrel 10 when the fabrication of the invention herein is completed, with the guidance furnished by slanted surface 134 of the tab 13 facilitating the objective of simple assembly; additionally, following injection or blood aspiration, it is only necessary to the rotate the barrel 10 and the sleeve 30, pull outward, and then rotate once again to reach the safe position, wherein the hypodermic needle 12 is covered and, furthermore, the protective cap 23 of the plunger 20 seals the front end of the sleeve 30 which also prevents hypodermic needle 12 protrusion from the guide groove 33 such that the overall structure is not only economical and capable of greater safety, but also has practical value in terms of production.

Figure 8:
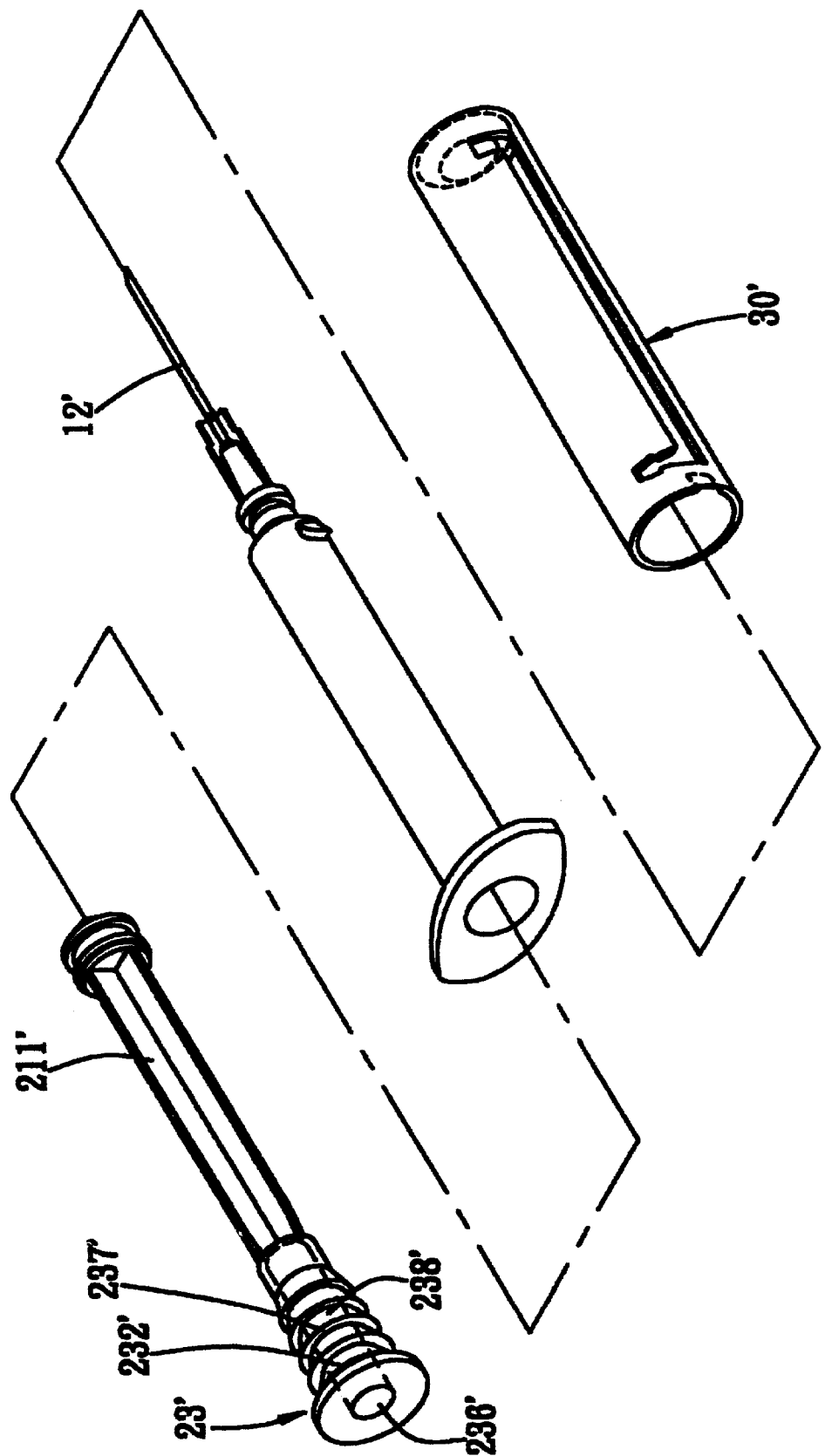
FIG. 8 is an exploded drawing of the second preferred embodiment of the invention herein.

Referring to FIG. 8 and FIG. 9, in the second preferred embodiment of the invention herein, the said protective cap 23' is fabricated as a hollow tubular construct and, furthermore, has an insertion hole 236' formed inside, with a number of latch rings 237' disposed along its interior side of the circumferential surface of the groove 232'; the said latch rings 237' are aligned with a press plate 231' having a larger diameter and, furthermore, the diameter of the latch rings 237' gradually decrease as they extend inward and a guide surface 238' is formed around the circumference; as indicated in FIG. 10, when the protective cap 23' is broken and, furthermore, to be inserted into the other end of the sleeve 30', since the connection point of the protective cap 23' and the plunger elements 21' is only that of the tubular wall thickness, breaking it is relatively easy; forcing the said latch rings 237' against the mounting ring 32' causes the mounting ring 32' to become ensconced in the groove 232' and the hypodermic needle 12' to become ensheathed into the insertion hole 236' and, as such, this structure is not only capable of positioning the protective cap 23', but also the protective cap 23' houses the hypodermic needle 12' and keeps it from becoming exposed.

Figure 11:
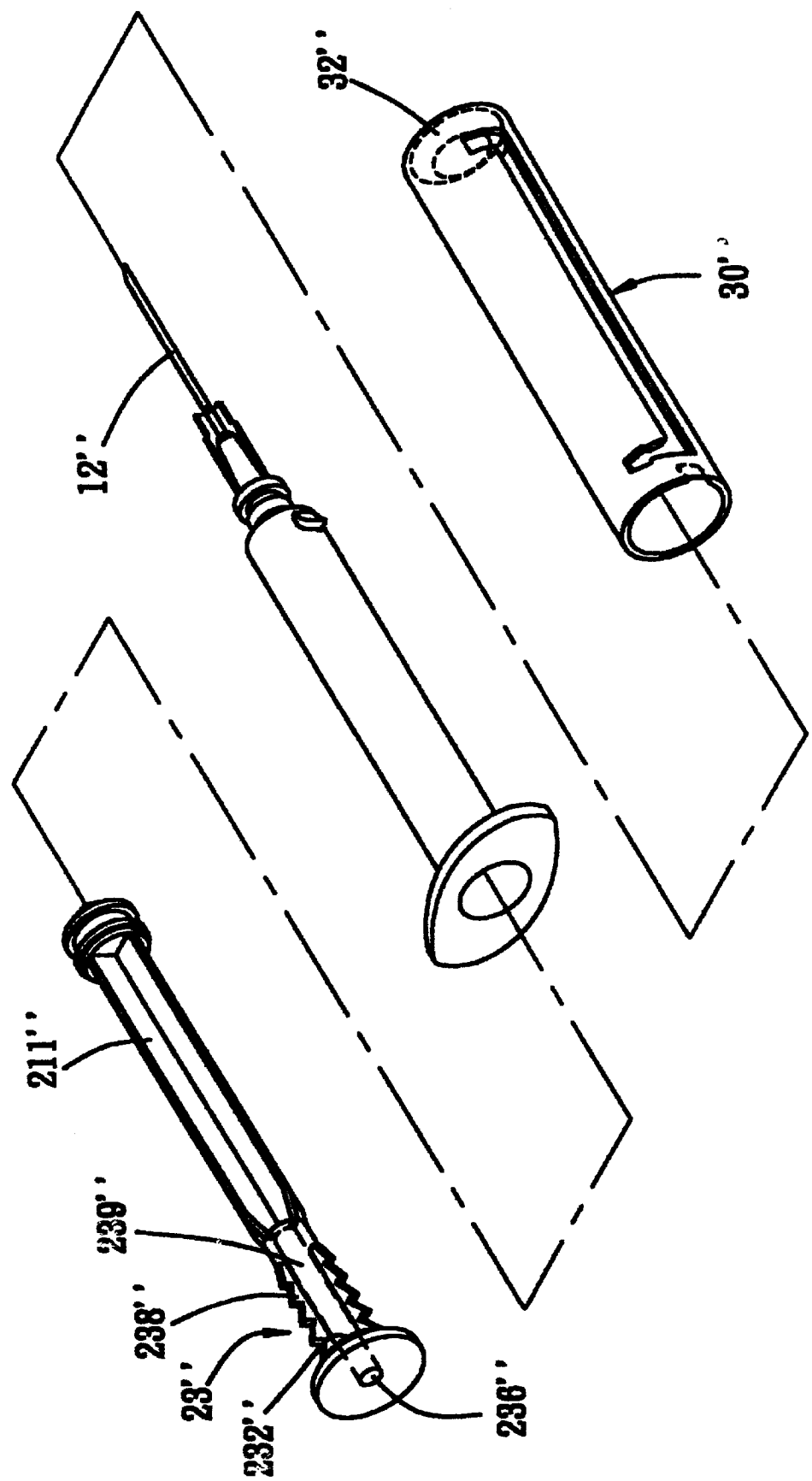
FIG. 11 is an exploded drawing of the third preferred embodiment of the invention herein.

Referring to FIG. 11, the said protective cap 23" is fabricated as a hollow tubular construct and, furthermore, has an insertion hole 236" formed within the interior section as well as a tube 239" formed inside the groove 232"; the connection point of the tube 239" and the plunger elements 211" is only that of the tubular wall thickness of the tube 239"; a number of ribs 237" are disposed lengthwise along the outer periphery of the said tube 239", a number of latch serrations 238" are formed on the said ribs 237" and, furthermore, the latch serrations 238" nearest the press plate 231" are of greater height, with the height of the latch serrations 238" gradually decreasing as they proceed inward, such that when the protective cap 23" is broken and, furthermore, about to be inserted into the other end of the sleeve 30", forcing the said latch serrations 238" against the mounting ring 32" causes the mounting ring 32" to become ensconced in the groove 232" and the hypodermic needle 12" become ensheathed into the insertion hole 236" and, as such, the said structure is not only capable of positioning the protective cap 23", but the protective cap 23" also houses the hypodermic needle 12" and keeps it from becoming exposed.

In summation of the foregoing section, since the invention herein is more progressive and practical than products in the same category and an investigation of the domestic and foreign technological materials and documents relating to such structures revealed no existent equivalent structure prior to its disclosure, the present invention meets the requirements of original patent applications and is hereby submitted for review and the granting of the commensurate patent rights.

However, the preceding description only relates to the preferred embodiments that are cited as workable examples of the present invention and, therefore, all modifications and adaptations based on the structure disclosed in the detailed description of the preferred embodiments and the claims thereof shall remain within the scope and claims of the invention herein.

What is claimed is:

1. An improved structure safety syringe, wherein the said syringe consists of a barrel of a hollow cylindrical construction having a plunger inserted in a plunger opening and, furthermore, a hypodermic needle is installed at one end of the said barrel; a sleeve of a hollow tubular construction having a sleeve opening inside is slipped over the exterior section of the said barrel; a tab is disposed near the said hypodermic needle on the two sides of the circumferential surface of the said barrel; a guide slot is disposed lengthwise along the walled face of the said sleeve; a limit slot extends from along the circumferential surface at the two ends of the said guide slot, with the guiding action of the said guide slots enabling a retraction and extension movement by the said barrel and the said sleeve and, furthermore, utilizing the said limit slot fixes the position after the movement of the said barrel and the said sleeve; and a protective cap proximal to the force application end of the said plunger can be broken off at the appropriate time, enabling the insertion of the broken off said protective cap into the other end of the said sleeve, and the innovations are:

the said barrel has the said tab which is of a trapezoidal shape with an insertion end formed at one extremity and a catch section formed at the other extremity and, furthermore, the width of the said catch section is larger than that of the said insertion end and an angled leading surface is formed on two sides, with the said angled leading surface gradually expanding outward in angle as it proceeds from the said insertion end to the said catch end; a slanted surface is formed on the top surface of the said tab and the said slanted surface is aligned with lower side of the said hypodermic needle, the said sleeve, wherein an insertion section is formed at the interior end of the said limit slot and a stop section projects towards the said limit slot in each of the openings between the said insertion sections and said limit slots and, furthermore, enabling the width between the two said stop sections to be smaller than the width of the said barrel catch end such that the said tab is insertable between the said two stop sections and remains ensconced in a fixed position in the said insertion sections and, furthermore, a circular binding-type mounting ring is formed at the said insertion section along the circumferential surface inside the other end of the said sleeve, the said plunger, the said protective cap of which has a groove formed on the interior lateral surface of a press plate such that when the said protective cap is broken off and inserted into the other end of the said sleeve, the engagement of the said groove and the said mounting ring enables the said protective cap to become fixed in position.

2. As mentioned in claim 1 of the improved structure safety syringe invention herein, a number of plunger elements are formed on the said protective cap of the said plunger, of which a latch section projects outward from one of the said elements, the said sleeve has a catch slot of an appropriate length and, furthermore, is open in a single direction as formed in the circumferential surface at one end of the said mounting ring such that when the said protective cap is broken and, furthermore, inserted into the other end of the said sleeve, the said latch section is engaged in the said catch slot, thereby enabling the positioning of the said protective cap.

3. As mentioned in claim 1 of the improved structure safety syringe invention herein, the said protective cap is fabricated as a hollow tubular construct and, furthermore, has an insertion hole formed inside, with a number of latch rings disposed along the inner side of the circumferential surface of a groove; the said latch rings are aligned with a press plate having a larger diameter and, furthermore, the diameter of the said latch rings gradually decrease as they extend inward and a guide surface is formed around the circumference; when the said protective cap is broken and, furthermore, to be inserted in the other end of the said sleeve, forcing the said latch rings against the said mounting ring causes the said mounting ring to become ensconced in the said groove and the said hypodermic needle to become ensheathed in the said insertion hole, thereby enabling the positioning of the said protective cap.

4. As mentioned in claim 1 of the improved structure safety syringe invention herein, the said protective cap is fabricated as a hollow tubular construct and, furthermore, has an insertion hole formed within the interior section as well as a tube formed inside the groove; a number of ribs are disposed lengthwise along the outer periphery of the said tube, a number of latch serrations are formed on the said ribs and, furthermore, the said latch serrations nearest the said press plate are of greater height and the height of the said latch serrations gradually decrease as they proceed inward, such that when the said protective cap is broken and, furthermore, about to be inserted into the other end of the said sleeve, forcing the said latch serrations against the said mounting ring causes the said mounting ring to become ensconced in the said groove and the said hypodermic needle to become ensheathed in the said insertion hole, thereby enabling the positioning of the said protective cap.

5. As mentioned in claim 1 of the improved structure safety syringe invention herein, an angled leading surface aligned with the said guide slot is formed on the interior annular surface at one end of the said sleeve opening of the said sleeve and, furthermore, enabling the said angled leading surface to gradually increase outward in angle.

* * * * *